United States Patent [19]

Singh

[11] Patent Number: 5,603,916
[45] Date of Patent: Feb. 18, 1997

[54] 3 5-BIS ALKANOYL AMINO-2 4 6-TRIIODOBENZYL ESTERS

[75] Inventor: Baldev Singh, Collegeville, Pa.

[73] Assignee: Nano Systems L.L.C., Collegeville, Pa.

[21] Appl. No.: 447,132

[22] Filed: May 22, 1995

[51] Int. Cl.$^6$ .................... A61K 49/04; C07C 229/00; C07C 69/76
[52] U.S. Cl. .................... 424/9.45; 560/47; 560/103
[58] Field of Search ................ 424/5, 9.45; 560/47, 560/103

[56] References Cited

U.S. PATENT DOCUMENTS

| | | | |
|---|---|---|---|
| 4,022,814 | 5/1977 | Newton | 260/463 |
| 4,175,544 | 11/1979 | Newton | 128/654 |
| 4,567,034 | 1/1986 | Charles et al. | 424/5 |
| 5,318,767 | 6/1994 | Liverside et al. | 424/4 |
| 5,488,133 | 1/1996 | Singh et al. | 424/9.45 |

Primary Examiner—Gary Geist
Assistant Examiner—Rosalynd A. Williams
Attorney, Agent, or Firm—Rudman & Balogh

[57] ABSTRACT

This invention relates to methods of x-ray diagnostic imaging the blood pool, liver, spleen and/or lymph system of a mammal comprising administering a contrast effective amount of a contrast agent having the structure:

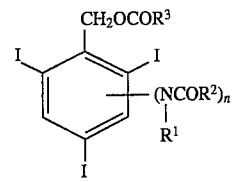

wherein:

n is 2;

$R^1$ is H or alkyl containing from 1 to 4 carbon atoms;

$R^2$ is H, alkyl containing from 1 to 4 carbon atoms, aryl or heteroaryl;

and $R^3$ is alkyl containing from 1 to 18 carbon atoms.

This invention further relates to novel contrast agents having the above structure wherein $R^1$ is H and $R^2$ and $R^3$ are $CH_3$ to x-ray contrast compositions comprising such agents, and to method of x-ray diagnostic imaging utilizing such agents.

11 Claims, No Drawings

3 5-BIS ALKANOYL AMINO-2 4 6-TRIIODOBENZYL ESTERS

FIELD OF INVENTION

This invention relates to methods of x-ray diagnostic imaging the blood pool, liver, spleen and/or lymph system of a mammal employing particulate compounds as a contrast agent, and to certain novel compounds useful as contrast agents in x-ray contrast compositions and methods of diagnostic imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson, et al, *Pharmaceuticals in Medical Imaging*, 1990, MacMillan Publishing Company.

Great Britain Patent No. 889339 describes an x-ray contrast composition comprising an iodinated benzoic acid derivative and a non-toxic carrier. The compounds collect in the gall bladder.

U.S. Pat. No. 3,097,228 describes derivatives of 2,4,6-triiodobenzoyloxyalkanoic acids having the structure:

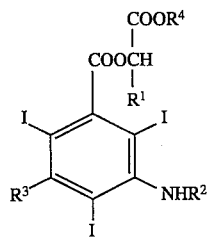

wherein $R^1$ is H or lower alkyl; $R^2$ is H or lower alkanoyl; $R^3$ is H or lower alkanoylamino and $R^4$ is lower alkyl. The agents are useful as x-ray contrast agents for visualizing the gall bladder (cholecystography) when administered orally, in the free acid form or in the form of a non-toxic salt, or intravenously, in the form of a water soluble, nontoxic salt. Example 15 therein describes ethyl 2-[3,5-bis(acetylamino)]-2,4,6-triiodobenzoyloxy) hexanoate,

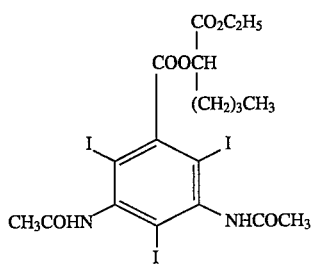

Bacon et al, commonly assigned U.S. patent application Ser. No. 07/990,987 filed Dec. 16, 1992, now U.S. Pat. No. 5,332,679 describes iodinated aroyloxy esters which are useful as contrast agents in x-ray imaging compositions and methods. However, all of the compounds described by Bacon et al feature an ester group linked through a $C_2$ or higher alkylene group to another ester group on an iodinated aromatic ring.

U.S. Pat. No. 3,128,301 by Larsen et al describes x-ray contrast agents having the structure:

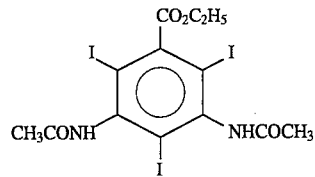

which contains a carboxylic ester group.

In "Preparation of 3,5-Diaminobenzyl Alcohol and Its Iodinated Derivatives," Hebbky and Polacek, Collection Czechoslov. Chem. Common, 1970, 35 (2), 667–74 the preparation the 3,5 diaminobenzyl alcohol precursor for a 3,5-bis(diacethylamino)-2,4,6-triodobenzyl chloride compound is disclosed.

U.S. Pat. No. 5,322,679 by Bacon et al describes nanoparticulate x-ray contrast agents having the structure:

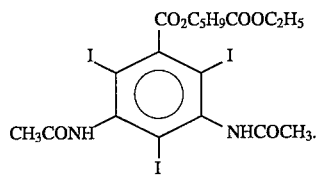

EP-A-498,482 describes nanoparticulate x-ray contrast compositions which have proven to be extremely useful in medical imaging. The compositions comprise particles of an organic x-ray contrast agent and a surface modifier adsorbed on the surface thereof and have an effective average particle size of less than 400 nm. The agents can be delivered to a specific tissue or fluid site, e.g., the blood pool, liver, spleen, kidney or lymph nodes. Example 8, therein describes a formulation comprising ethyl 2-[3,5-bis(acetylamino)]-2,4, 6-triiodobenzoyloxy) butyrate, i.e.,

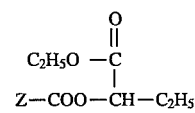

wherein (Z)-COO is the residue of diatrizoic acid.

However, it has been discovered that ethyl 2-(3,5-bis(acetylamino)-2,4,6-triiodobenzoyloxy) butyrate exhibits multiple crystal forms, i.e., polymorphs, e.g., when recrystallized from various solvents. The reasons that this behavior are not completely understood but, in any event, multiple crystal forms are disadvantageous for a variety of reasons. For example, the presence of multiple crystal forms renders scale up problematic due to the lack of reproducibility of the results obtained, including, e.g., in chemical manufacturing and in the milling process. Additionally, it has been found the nanoparticulate formulations of ethyl 2-[3,5-bis(acetylamino)]-2,4,6-triiodobenzoyloxy) butyrate do not exhibit good stability during autoclaving, i.e., conventional heat sterilization.

Consequently, it would be highly desirable to provide a poorly water soluble x-ray contrast agent having the advantages of ethyl 2-[3,5-bis(acetylamino)]-2,4,6-triiodobenzoyloxy) butyrate but which exhibits a consistent and reproducible crystal morphology, optimum hydrolysis, solubility and a high melting point is amenable to reproducible scale up and can be successfully heat sterilized by autoclaving to produce a stable and less toxic material.

It would be very useful to provide a contrast agent that hydrolyzes faster and results in faster systemic clearance.

SUMMARY OF THE INVENTION

I have discovered that certain compounds exhibit reproducibly consistent crystal morphology during manufacture and purification, optimum hydrolysis, solubility and a high melting point and thus are particularly amenable to reproduce as particulate contrast agents for use in methods of x-ray diagnostic imaging the blood pool, liver, spleen and lymphatic system of a mammal and particularly hydrolyzes quickly resulting in fast systemic clearance from the body. In a composition of matter aspect, I have discovered and synthesized novel compounds which are useful as contrast agents in x-ray diagnostic imaging compositions and methods.

More specifically, in accordance with this invention, there is provided a method of medical x-ray diagnostic imaging which comprises administering to the blood pool, liver, spleen or lymph system of a mammal a contrast-effective amount of a particulate contrast agent 3,5-bis(alkanoylamino)-2,4,6-triiodo benzyl esters) having structure 1:

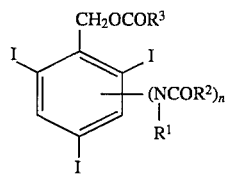

wherein: n is 2;
$R^1$ is H or alkyl containing from 1 to 4 carbon atoms;
$R^2$ is H, alkyl, aryl, or heteroaryl; and
$R^3$ is alkyl containing from 1 to 18 carbon atoms.

In another aspect, there are provided novel compounds having structure 1 above wherein $R^1$ is H and $R^2$ and $R^3$ are $CH_3$. This invention further provides an x-ray contrast composition comprising such novel compounds and a method for medical x-ray diagnostic imaging which comprises administering to a mammal an effective contrast-producing amount of the abovedescribed x-ray contrast composition.

It is an advantageous feature of this invention that methods of x-ray diagnostic imaging the blood pool, liver, spleen and lymphatic system are provided employing an x-ray contrast composition featuring a compound which exhibits a consistent crystal morphology during purification and thus is particularly amenable to reproducible scale up and has optimum hydrolysis, solubility and a high melting point.

It is another advantageous feature of this invention that x-ray contrast compositions are provided for blood pool, liver, spleen and lymphatic system imaging which exhibit improved visualization.

It is a particularly advantageous feature of this invention that the contrast agent hydrolyzes quickly and results in fast systemic clearance from the body.

Still another advantageous feature of this invention is that novel compounds are provided which find particular utility as particulate x-ray contrast agents.

DESCRIPTION OF PREFERRED EMBODIMENTS

In structure 1 above, $R^1$ is H or alkyl containing from 1 to 4 carbon atoms. The alkyl group may be linear or branched and most preferably is methyl. Examples of useful alkyl groups are methyl, ethyl, isopropyl, butyl and the like.

$R^2$ is H or alkyl as described above for $R^1$ and can also be aryl such as phenyl, tolyl anthracene and the like, or heteroaryl such as thiophene, benzofuran and the like.

$R^3$ is alkyl containing from 1 to 18 carbon atoms. Again the alkyl group can be linear or branched. Examples are methyl, ethyl, propyl, isobutyl, butyl, hexyl and the like.

The preferred compound of the invention has the structure 2:

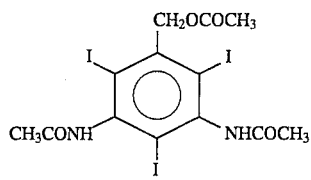

The compounds of this invention can be prepared by reacting 3,5-diaminobenzoic acid

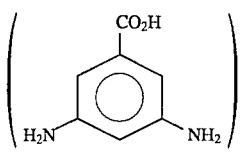

with lithium aluminum hydride ($LiAlH_4$) to form a compound having the structure

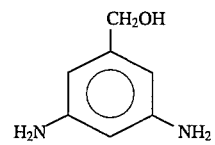

which is reacted with acetylchloride ($CH_3COCl$) or acetic anhydride ($Ac_2O$)) to form a compound having the structure

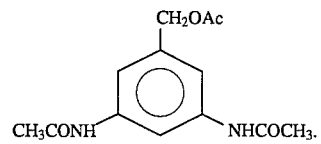

This compound is then treated with sodium iodide dichloride ($NaICl_2$) to form a compound having the formula

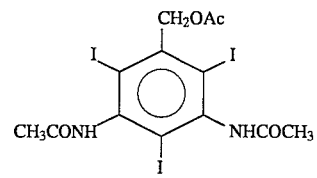

This compound is then treated first with sodium hydroxide (NaOH) and then with hydrochloric acid to form a compound having the formula

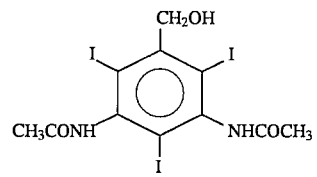

This compound is reacted with alkanoyl anhydride (($R^3CO$)$_2$) to form the compound with the structure

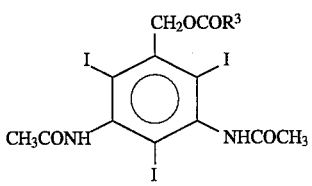

Solvents useful in the above reactions are dimethyl formamide (DMF) and the corresponding alkanolic acids ($R^3COH$). Temperatures can be from 25° C. to 50° C. The reactions can take place at an ambient pressure, although higher and lower pressures are contemplated.

The iodinated compounds can contain substituents which do not deleteriously affect the contrast-enhancing capability of the compound. For example, the alkyl and aryl groups in structure I above can be unsubstituted or substituted with various substituents which do not adversely affect the stability or efficacy of the compounds as x-ray contrast agents such as alkyl, cycloalkyl, aryl, aralkyl, alkoxy, hydroxy, acyloxy, halogen, such as chlorine, bromine and iodine, acylamino, carboalkoxy, carbamyl and the like.

When used as an x-ray contrast agent, the compound of this invention preferably comprises at least about 30%, more preferably at least 35%, and most preferably at least 40% iodine by weight.

In preferred embodiments, the compounds of this invention can be formulated into particulate x-ray contrast compositions, preferably nanoparticulate x-ray contrast compositions, as described in commonly-owned EP-a 498,482. Preferred compounds exhibit a melting point of greater than 150° C. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition. Preferred surface modifiers include nonionic surfactants.

In preferred embodiments, the surface modifier is a high molecular weight nonionic surfactant. Preferred surfactants include poloxamers such as Pluronic™ F68 and F108, which are block copolymers of ethylene oxide and propylene oxide, poloxamines, such as Tetronic™ 908 (also known as Poloxamine 908), which is a tetrafunctional block copolymer derived from sequential addition of propylene oxide and ethylene oxide to ethylenediamine, and dialkyl esters of sodium sulfosuccinic acid, such as dioctylsulfosuccinate sodium (DOSS). The concentrations of the surface modifier can vary from about 0.1–75%, preferably 1–60%, and more preferably 5–25% by weight based on the total combined weight of the contrast agent and surface modifier.

In preferred embodiments, the x-ray contrast composition in the form of surface modified nanoparticles can be associated with a cloud point modifier to further enhance stability during steam heat autoclaving, i.e., the cloud point modifier can reduce particle aggregation during heat sterilization. Preferred cloud point modifiers include nonionic cloud point modifiers, such as polyethylene glycols such as PEG 400, propylene glycol, ethanol, hydroxypropylcyclodextrin and glycerol; ionic cloud point modifiers, such as those described in U.S. Pat. No. 5,298,262 including dialkylesters of sodium sulfosuccinic acid such as the dioctylester of sodium sulfosuccinic acid (DOSS); and charged phospholipids, such as diacylphosphatidyl glycerol and dimyristoylphosphatidyl glycerol. The cloud point modifier can be present in an amount of 0.005–50%, preferably 0.01–30% and more preferably 0.05–20% by weight based on the total weight of the x-ray contrast composition.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1–99.9, preferably 2–45 and more preferably 10–30% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 20 to 450 mg of iodine per kilogram of body weight of the subject for many imaging applications. For some applications, e.g., lymphography, lower doses, e.g., 0.5–20 mg I/kg, can be effective. For blood pool imaging, the dose can range from 50 to 450 mg of iodine per kilogram of body weight and preferably from 100 to 250 mg of iodine per kilogram of body weight. For liver and spleen imaging, the dose can range from 1 to 20 mg/kg.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a convention manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intrathecal administration, intracisternal administration, oral administration, administration via inhalation, administration directly into a body cavity, e.g., arthrography, and the like.

In addition to preferred application, i.e., for blood pool, liver, spleen and lymph node imaging, the x-ray contract compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1—Preparation of Compound I

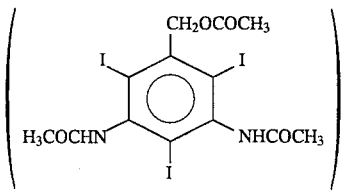

To a stirred solution of (3,5-diaminobenzoic acid)

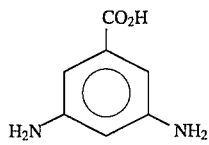

in dry 1,4-dioxane is added LiAlH$_4$. The solution is heated overnight at 90° C. then cooled to room temperature, work-up at the reaction mixture provides 3,5-diaminobenzyl alcahol which is acylated with acetic anhydride. The resulting triacetoxy intermediate is treated with sodium iodide dichloride in acetic acid at 50°–75° C. to yield compound I. The reaction scheme is as follows:

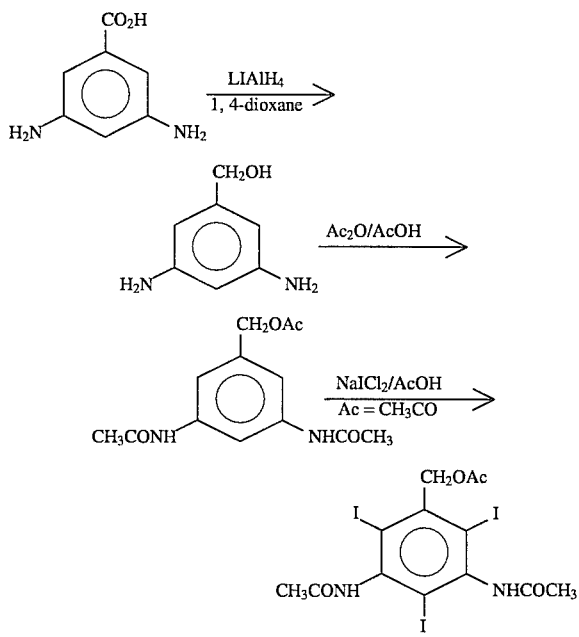

EXAMPLE 2—Preparation of Nanoparticulate Compound 1 Contrast Agent with Pluronic F680 Pluronic F108, or Tetronic T-908

Compound 1 is added to each of 3×1.5 oz brown glass bottles containing approximately 12 ml of zirconium silicate (1.1 mm dia.) beads in an amount sufficient to be 15% (w/v) of the final suspension. Bottle A contains 3% (w/v) Pluronic F-68. Bottle B contains 3% (w/v) Pluronic F108. Bottle C contains 3% (w/v) Tetronic T-908. The resulting suspensions are milled on a roller mill at approximately 150 rpm for a total of 9 days.

EXAMPLE 3—Preparation of Nanoparticulate Compound 1 Contrast Agent with Pluronic F108 and Blood Pool Imaging 15% Compound 1 can be milled with 4% Pluronic F-108 in the present of zirconium silicate (1.1 mm dia) beads for 3 days under aseptic conditions. No additional salts or surfactants are added.

This sample is examined for imaging efficacy. The sample is injected into white New Zealand rabbits at a dose of 3 ml/kg as a slow bolus injection. At times of 5, 15, 30, 60 and 120 min. post injection, the opacification of the liver, spleen, and blood pool as measured in the aorta and within the left ventricle is determined by computed tomography (CT) using a Toshiba 900S Imager CT scanner and associated software. Results from this analysis are expected to show that this formulation of Compound 1 has excellent blood pool opacification in excess of 30 min. followed by very good liver and very good spleen opacification for 120 min. Imaging at 24 hours post injection should show complete clearance from the blood with partial clearance from the liver and spleen.

EXAMPLE 4—Preparation of an Autoclavable Formulation of Nanoparticulate Compound 1 Contrast Agent with Pluronic F108 and PEG 400 and Lymphography Imaging Compound 1 is milled with zirconium silicate (1.1 mm dia) beads in the presence of Pluronic F-108 for 3 days. The final particle size is determined. At this point, sterile PEG 400 is added to the suspension such that at completion, the formulation contains 15% (w/v) WIN 70146, 3% (w/v) Pluronic F-108, and 10% (w/v) PEG 400. This formulation is then autoclaved under standard conditions, i.e., 121° C. for 20 min.

This formulation is evaluated for both blood pool and lymphographic imaging in New Zealand White Rabbits using the above-described protocol (3 ml/kg) for blood pool imaging and 2 injections (0.25 ml) per paw for lymphography. The results should indicate that Compound 1 is capable of blood pool opacification to at least 30 min. and is an excellent lymphography agent affording the highest level of opacification noted to date in this indication. Scanning is carried out using a Toshiba 900S Imager CT scanner and image density is calculated from iodinated standards imaged simultaneously with the animals.

The invention has been described in detail with particular reference to certain preferred embodiments thereof, but it will be understood that variations and modifications can be effected within the spirit and scope of the invention.

I claim:

1. A compound having the structure:

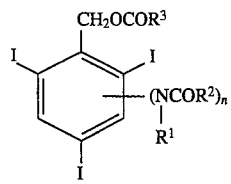

wherein:

n is 2;

R$^1$ is H or alkyl containing from 1 to 4 carbon atoms;

R$^2$ is H, alkyl containing from 1 to 4 carbon atoms, aryl or heteroaryl wherein aryl is phenyl, tolyl or anthracene and heteroaryl is thiophene or benzofuran; and R$^3$ is alkyl containing from 1 to 18 carbon atoms.

2. The compound of claim 1 wherein R$^1$ is H and R$^2$ is CH$_3$.

3. The compound of claim 1 wherein R$^3$ is methyl.

4. The compound having the structure:

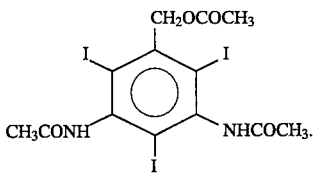

5. A method of medical x-ray diagnostic imaging the blood pool, liver, spleen, or lymph system of a mammal comprising administering to the mammal a contrast effective amount of a compound having the structure:

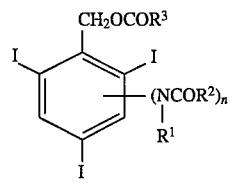

wherein:

n is 2;

R$^1$ is H or alkyl containing from 1 to 4 carbon atoms;

R$^2$ is H, alkyl containing from 1 to 4 carbon atoms, aryl or heteroaryl wherein aryl is phenyl, tolyl or anthracene and heteroaryl is thiophene or benzofuran; and R$^3$ is alkyl containing from 1 to 18 carbon atoms.

6. The method of claim 5 wherein R$^1$ is H and R$^2$ is CH$_3$.

7. The method of claim 5 wherein R$^3$ is methyl.

8. The method of claim 5 wherein the compound has the structure

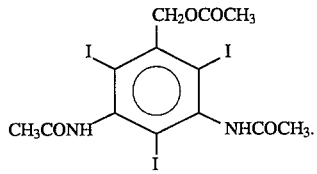

9. An x-ray contrast composition comprising the compound of claim 1.

10. The x-ray contrast composition of claim 9 further including a pharmaceutically acceptable carrier.

11. A method for medical x-ray diagnostic imaging which comprises administering to the body of a mammal a contrast effective amount of the x-ray contrast composition of claim 9.

* * * * *